(12) United States Patent
Chittibabu et al.

(10) Patent No.: US 7,220,914 B2
(45) Date of Patent: May 22, 2007

(54) ZWITTERIONIC COMPOUNDS AND PHOTOVOLTAIC CELLS CONTAINING SAME

(75) Inventors: Kethinni G. Chittibabu, Nashua, NH (US); Savvas Hadjikyriacou, Tyngsboro, MA (US); David Waller, Lexington, MA (US)

(73) Assignee: Konarka Technologies, Inc., Lowell, MA (US)

( * ) Notice: Subject to any disclaimer, the term of this patent is extended or adjusted under 35 U.S.C. 154(b) by 16 days.

(21) Appl. No.: 11/000,276

(22) Filed: Nov. 30, 2004

(65) Prior Publication Data
US 2005/0211292 A1 Sep. 29, 2005

Related U.S. Application Data

(60) Provisional application No. 60/526,373, filed on Dec. 1, 2003.

(51) Int. Cl.
*H01L 31/00* (2006.01)
(52) U.S. Cl. .................. 136/263; 564/86; 564/98; 548/335.5; 548/342.1; 562/37; 562/113
(58) Field of Classification Search ............. 136/263, 136/252, 256; 257/40, 431; 429/111; 548/335.5, 548/342.1; 562/37, 113; 564/86, 98
See application file for complete search history.

(56) References Cited

U.S. PATENT DOCUMENTS

| 2,230,965 | A | * | 2/1941 | Orem ..................... 562/104 |
| 3,925,262 | A | * | 12/1975 | Laughlin et al. .......... 510/345 |
| 5,192,405 | A | * | 3/1993 | Petersen et al. .......... 204/451 |
| 5,683,832 | A | | 11/1997 | Bonhote et al. |
| 5,728,839 | A | * | 3/1998 | Herrmann et al. ......... 548/103 |
| 5,827,602 | A | | 10/1998 | Koch et al. |
| 6,376,765 | B1 | | 4/2002 | Wariishi et al. |
| 2002/0009635 | A1 | | 1/2002 | Michot et al. |
| 2002/0009650 | A1 | | 1/2002 | Michot et al. |
| 2002/0102380 | A1 | | 8/2002 | Michot et al. |
| 2003/0052310 | A1 | | 3/2003 | Michot et al. |
| 2003/0066988 | A1 | | 4/2003 | Michot et al. |
| 2003/0087151 | A1 | | 5/2003 | Hamrock |
| 2003/0188776 | A1 | | 10/2003 | Li et al. |

FOREIGN PATENT DOCUMENTS

EP 1271581 A2 1/2003
JP 2002-367426 A * 12/2002

* cited by examiner

*Primary Examiner*—Nam Nguyen
*Assistant Examiner*—Jeffrey Barton
(74) *Attorney, Agent, or Firm*—Fish & Richardson P.C.

(57) ABSTRACT

Zwitterionic compounds, photovoltaic cell charge carrier layers containing such compounds, photovoltaic cells including such charge carrier layers, and related methods are disclosed.

57 Claims, 2 Drawing Sheets

ZWITTERIONIC COMPOUNDS AND PHOTOVOLTAIC CELLS CONTAINING SAME

CROSS-REFERENCE TO RELATED APPLICATION

This application claims priority under 35 U.S.C. §119(e)(1) to U.S. Ser. No. 60/526,373, filed Dec. 1, 2003, and entitled "Zwitterionic Compounds and Photovoltaic Cells Containing Same", which is hereby incorporated by reference.

TECHNICAL FIELD

The invention relates to zwitterionic compounds, photovoltaic cell charge carrier layers containing such compounds, photovoltaic cells including such charge carrier layers, and related methods.

BACKGROUND

Photovoltaic cells, sometimes called solar cells, can convert light, such as sunlight, into electrical energy. One type of photovoltaic cell is a dye-sensitized solar cell (DSSC).

Referring to FIG. 1, is a DSSC 100 includes a charge carrier layer 140 (e.g., including an electrolyte, such as an iodide/iodine solution) and a photosensitized layer 145 (e.g., including a semiconductor material, such as $TiO_2$ particles) disposed between an electrode 101 and a counter electrode 111. Photosensitized layer 145 also includes a photosensitizing agent, such as a dye. In general, the photosensitizing agent is capable of absorbing photons within a wavelength range of operation (e.g., within the solar spectrum). Electrode 101 includes a substrate 160 (e.g., a glass or polymer substrate) and an electrically conductive layer 150 (e.g., an ITO layer or tin oxide layer) disposed on substrate 160. Counter electrode 111 includes a substrate 110, an electrically conductive layer 120 (e.g., ITO layer or tin oxide layer), and a layer 130 formed of a material (e.g., platinum) that catalyzes a redox reaction in charge carrier layer 140. Electrode 101 and counter electrode 111 are electrically connected across an external electrical load 170.

During operation, in response to illumination by radiation in the solar spectrum, DSSC 100 undergoes cycles of excitation, oxidation, and reduction that produce a flow of electrons across load 170. Incident light excites photosensitizing agent molecules in photosensitized layer 145. The photoexcited photosensitizing agent molecules then inject electrons into the conduction band of the semiconductor in layer 145, which leaves the photosensitizing agent molecules oxidized. The injected electrons flow through the semiconductor material, to electrically conductive layer 150, then to external load 170. After flowing through external load 170, the electrons flow to layer 120, then to layer 130 and subsequently to layer 140, where the electrons reduce the electrolyte material in charge carrier layer 140 at catalyst layer 130. The reduced electrolyte can then reduce the oxidized photosensitizing agent molecules back to their neutral state. The electrolyte in layer 140 can act as a redox mediator to control the flow of electrons from counter electrode 111 to working electrode 101. This cycle of excitation, oxidation, and reduction is repeated to provide continuous electrical energy to external load 170.

SUMMARY

The invention relates to zwitterionic compounds, photovoltaic cell charge carrier layers containing such compounds, photovoltaic cells including such charge carrier layers, and related methods.

In one aspect, the invention features a zwitterionic compound that has the formula:

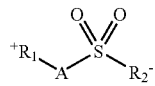

$R_2$ is an anoinic moiety with the formula:

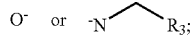

$R_1$ is a cationic heterocyclic moiety, a cationic ammonium moiety, a cationic guanidinium moiety, or a cationic phosphonium moiety. A is $(C(R_3)_2)_n$. n is zero or greater. Each $R_3$ is independently H or a carbon-containing moiety selected from $C_x$ alkyl, cycloalkyl, heterocyclyl, $C_{x+1}$ alkenyl, $C_{x+1}$ alkynyl and aryl. The carbon-containing moiety optionally is substituted with one or more halo. x is at least 1.

In another aspect, the invention features a photovoltaic cell charge carrier layer that includes a zwitterionic compound with the formula:

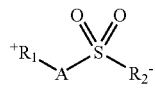

$R_2$ is an anionic moiety with the formula:

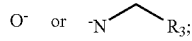

$R_1$ is a cationic heterocyclic moiety, a cationic ammonium moiety, a cationic guanidinium moiety, or a cationic phosphonium moiety. A is $(C(R_3)_2)_n$. n is zero or greater. Each $R_3$ is independently H, or a carbon-containing moiety selected from $C_x$ alkyl, cycloalkyl, heterocyclyl, $C_{x+1}$ alkenyl, $C_{x+1}$ alkynyl and aryl. The carbon-containing moiety optionally is substituted with one or more halo. x is at least 1.

In a further aspect, the invention features a photovoltaic cell that includes two electrodes and a charge carrier layer between the electrodes. The charge carrier layer includes an electrolyte and a zwitterionic compound with the formula:

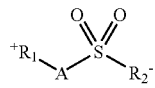

$R_2$ is an anionic moiety with the formula:

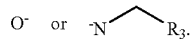

$R_1$ is a cationic heterocyclic moiety, a cationic ammonium moiety, a cationic guanidinium moiety, or a cationic phosphonium moiety. A is $(C(R_3)_2)_n$. n is zero or greater. Each $R_3$ is independently H, or a carbon-containing moiety selected from $C_x$ alkyl, cycloalkyl, heterocyclyl, $C_{x+1}$ alkenyl, $C_{x+1}$ alkynyl and aryl. The carbon-containing moiety optionally is substituted with one or more halo. x is at least 1.

Embodiments can include one or more of the following features.

n can be, for example, at least 1 and/or at most 20 (e.g., at most 10, at most 5).

x can be, for example, at most 20 (e.g., at most 15, at most 10).

$R_1$ can be, for example, a cationic nitrogen-substituted heterocyclic moiety with at least two nitrogen atoms, or an alkyl substituted cationic ammonium moiety.

In some embodiments, $R_1$ is a cationic nitrogen-substituted heterocyclic moiety, a cationic alkyl substituted ammonium moiety, a cationic guanidinium moiety, or a cationic phosphonium moiety; and each $R_3$ is independently H, or a $C_1$–$C_6$ alkyl that is optionally substituted with one or more halo.

In certain embodiments, n is 1–4; $R_1$ is an alkyl imidazolium, piperidinium, pyridinium, morpholinium, pyrimidinium, pyridazinium, pyrazinium, pyrazolium, pyrrolinium, thiazolium, oxazolium, triazolium pentalkyl guanidinium, or asymmetric tetraalkylammonium; and each $R_3$ is independently H, or a $C_1$–$C_6$ alkyl that is optionally substituted with one or more F.

In some embodiments, n is 1–4; $R_1$ is alkyl imidazolium, pyridinium, pyridazinium, or pyrazinium; and $R_3$ is a Me that is optionally substituted with one or more F.

In certain embodiments, n is 2 or 3; $R_1$ is alkyl imidazolium; and $R_3$ is $CF_3$.

In some embodiments, the zwitterionic compound has the formula:

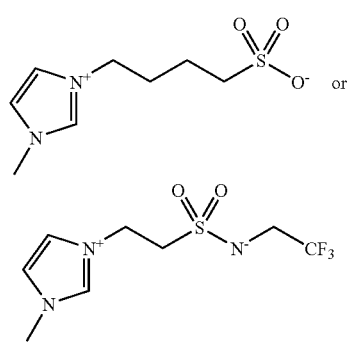

or

A charge carrier layer can further include an electrolyte (e.g., a lithium salt). The electrolyte in a charge carrier layer can be in the form a complex. The charge carrier layer can include, for example, at least about 10 volume fraction of the complex and/or at most about 60 volume fraction of the complex.

A charge carrier layer can further include a redox system. The charge carrier layer can include, for example, at least about 10 volume fraction of the redox system and/or at most about 60 volume fraction of the redox system.

A charge carrier layer can further include a solvent. The charge carrier layer can include, for example, at least about five volume fraction of the solvent and/or at most about 70 volume fraction of the solvent.

Embodiments can provide one or more of the following advantages.

In some embodiments, a charge carrier layer containing one or more zwitterionic compounds can have a relatively high viscosity. This can assist in reducing (e.g., preventing) the undesired flow of one or more constituents of the charge carrier layer (e.g., to locations within the photovoltaic cell, to locations outside of the photovoltaic cell).

In certain embodiments, the presence of one or more zwitterionic compounds in a charge carrier layer can reduce the ability of one or more constituents contained in the charge carrier layer to undergo undesired reactions with components in the photovoltaic cell. As an example, the presence of the zwitterionic compound(s) can reduce the ability of an ion (e.g., a cation, such as lithium) to undergo undesired chemical reactions with a phosensitizing agent (e.g., a dye) contained within the photovoltaic cell. As another example, the presence of the zwitterionic compound(s) can reduce the ability of an ion (e.g., an anion) to undergo undesired chemical reactions with one or more counterelectrode materials (e.g., platinum).

In some embodiments, the presence of one or more zwitterionic compounds in a charge carrier layer can reduce migration of charge within the charge carrier layer. This can improve the performance of the photovoltaic cell and/or increase the useful lifetime of the photovoltaic cell.

In certain embodiments, the presence of one or more zwitterionic compounds in a charge carrier layer can allow for enhanced ability to control selective ion conduction within the charge carrier layer, which can improve the performance of the photovoltaic cell.

DETAILED DESCRIPTION

Figure 1:
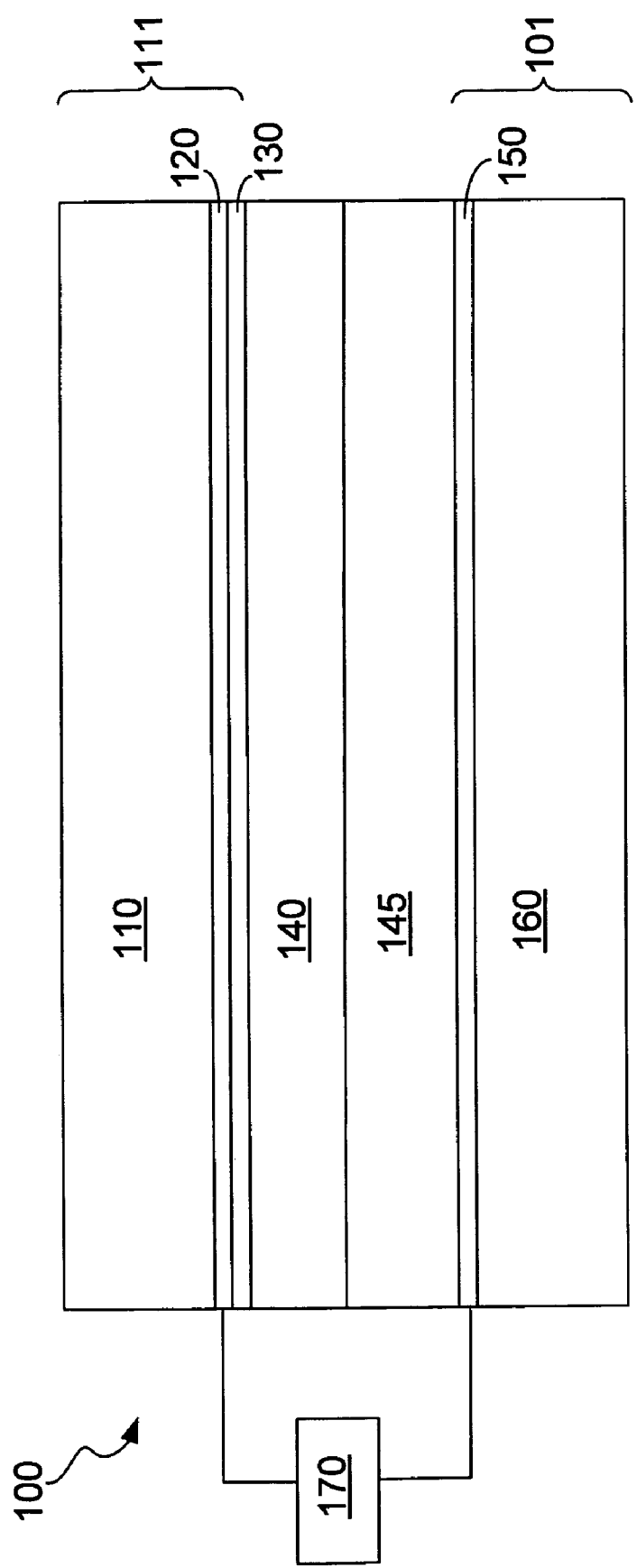
FIG. 1 is a cross-sectional view of an embodiment of a photovoltaic cell.

The invention provides zwitterionic compounds that can, for example, be used in the charge carrier layer 140 of photovoltaic cell 100. In general, the zwitterionic compounds have the formula:

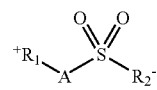

$R_1$ is a cationic heterocyclic moiety, a cationic ammonium moiety, a cationic guanidinium moiety, or a cationic phosphonium moiety. $R_1$ can be unsubstituted or substituted (e.g., alkyl substituted, alkoxy substituted, poly(ethyleneoxy) substituted, nitrogen-substituted). Examples of cationic substituted heterocyclic moieties include cationic nitrogen-substituted heterocyclic moieties (e.g., alkyl imidazolium, piperidinium, pyridinium, morpholinium, pyrimidinium, pyridazinium, pyrazinium, pyrazolium, pyrrolinium, thiazolium, oxazolium, triazolium).

Examples of cationic substituted ammonium moieties include cationic alkyl substituted ammonium moieties (e.g., symmetric tetraalkylammonium).

Examples of cationic substituted guanidinium moieties include cationic alkyl substituted guanidinium moieties (e.g., pentalkyl guanidinium).

$R_2$ is an anionic moiety that can be:

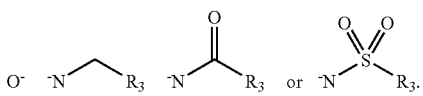

where $R_3$ is H or a carbon-containing moiety selected from $C_x$ alkyl, $C_{x+1}$ alkenyl, $C_{x+1}$ alkynyl, cycloalkyl, heterocyclyl and aryl; and x is at least 1 (e.g., two, three, four, five, six, seven, eight, nine, 10, 11, 12, 13, 14, 15, 16, 17, 18, 19, 20). In some embodiments, a carbon-containing moiety can be substituted (e.g., halo substituted).

A is $(C(R_3)_2)_n$, where: n is zero or greater (e.g., one, two, three, four, five, six, seven, eight, nine, 10, 11, 12, 13, 14, 15, 16, 17, 18, 19, 20); and each $R_3$ is independently as described above.

As referred to herein, the term "alkyl" means an unsaturated carbon-containing chain. An alkyl can be a straight chain or branched chain. An alkyl may be unsubstituted or substituted (e.g., halo substituted, nitrile substituted).

As used herein, the term "alkenyl" refers to a carbon-containing moiety having at least one carbon-carbon double bond. An alkenyl can be a straight chain or branched chain. An alkenyl may be unsubstituted or substituted (e.g., halo substituted).

As referred to herein, the term "alkynyl" means a carbon-containing chain having at least one carbon-carbon triple bond. An alkynyl can be a straight chain or branched chain. An alkynyl may be unsubstituted or substituted (e.g., halo substituted).

As used herein, the term "cycloalkyl" refers to a carbon-containing moiety that includes at least one non-aromatic cyclic group. A cyclic group can be nonsaturated, fully saturated or partially unsaturated. A cyclic group can be unsubstituted or substituted (e.g., halo substituted, nitrile substituted). In general, the number of carbon atoms contained in a cyclic group can be selected as desired. Typically, a cyclic group includes at least three carbon atoms (e.g., four carbon atoms, five carbon atoms, six carbon atoms, seven carbon atoms, eight carbon atoms, nine carbon atoms, 10 carbon atoms, 11 carbon atoms, 12 carbon atoms). Examples of cyclic groups include cyclopropyl, cyclobutyl, cyclopentyl, cyclopentenyl, cyclohexyl, cyclohexenyl, cycloheptyl and cyclooctyl.

As referred to herein, the term "heterocyclyl" refers to a nonaromatic monocyclic, bicyclic or tricyclic ring system. Examples of heterocyclyls include 5–8 membered monocyclic ring systems, 8–12 membered bicyclic ring systems, and 11–14 membered tricyclic ring system. In some embodiments, a monocyclic ring system has 1–3 heteroatoms. In certain embodiments, a bicyclic ring system has 1–6 heteroatoms. In some embodiments, a tricyclic ring system has 1–9 heteroatoms. Examples of heteroatoms include O, N, and S. Examples of heterocyclyl groups include piperazinyl, pyrrolidinyl, dioxanyl, morpholinyl, and tetrahydrofuranyl.

As referred to herein, the term "aryl" means a carbon-containing moiety having at least one aromatic ring. For example, an aryl can contain at least one 6-carbon monocyclic aromatic ring and/or at least one 10-carbon bicyclic aromatic ring system. Zero, one, two, three or four of the atoms in each ring can be substituted (e.g., halo substituted, alkyl substituted, alkoxy substituted, nitrile substituted, carboxy substituted).

In some embodiments, an aryl can be a heteroaryl. The term "heteroaryl" refers to a carbon-containing moiety that has at least one aromatic ring with at least one non-carbon atom (e.g., O, S, N) in the ring. Examples of heteroaryls include: aromatic 5–8 membered monocyclic rings with at least one O, S and/or N in the ring; 8–12 membered bicyclic rings with at least one O, S and/or N in the ring; and 11–14 membered tricyclic rings with at least one O, S and/or N in the ring. Generally, for monocyclic ring systems, the number of non-carbon atoms in the ring is one, two or three; for bicyclic rings, the number of non-carbon atoms in the ring is one, two, three, four, five or six; for tricyclic rings, the number of non-carbon atoms in the ring is one, two, three, four, five, six, seven, eight or nine. The atoms in a ring may be unsubstituted or substituted (e.g., halo substituted, alkyl substituted, alkoxy substituted, poly(ethyleneoxy) substituted). Examples of heteroaryl groups include pyridyl, furyl, furanyl, imidazolyl, benzimidazolyl, pyrimidinyl, thiophenyl, thienyl, quinolinyl, indolyl, and thiazolyl.

As used herein, the term "halo" refers to F, Cl, Br or I.

As used herein, the term "Me" refers to methyl.

In some embodiments, the zwitterionic compound has the formula:

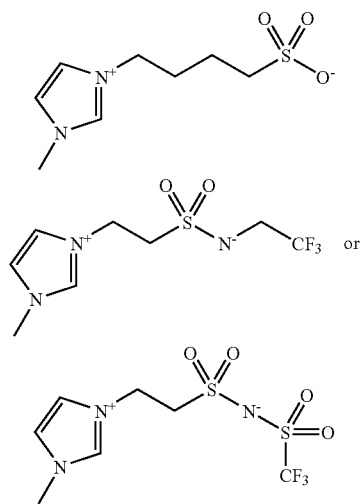

In addition to one of more zwitterionic compounds, charge carrier layer 140 includes a charge carrier material that facilitates the transfer of electrical charge from a ground potential or a current source to photosensitized layer 145.

Charge carrier materials include solvent-based liquid electrolytes, ionic liquids polyelectrolytes, polymeric electrolytes, solid electrolytes, n-type and p-type transporting materials (e.g., conducting polymers) and gel electrolytes. Other choices for charge carrier media are possible. For example, charge carrier layer 140 can include a lithium salt can have the formula LiX, where X is an iodide, bromide, chloride, perchlorate, thiocyanate, trifluoromethyl sulfonate, hexafluorophosphate, $BF_4^-$ or trifluoromethanesulfonimide.

In embodiments in which layer 140 includes a polymeric electrolyte, the polymeric electrolyte can generally include any polymeric material that is cationic or zwitterionic, such as poly(vinyl imidazolium halide). Layer 140 can further include lithium iodide and/or polyvinyl pyridinium salts Examples of solid electrolytes include lithium iodide, pyridimum iodide, substituted imidazolium iodide, and guanidium salts.

Polyelectrolytes can include from about 5% to about 95% (e.g., from about 5% to about 60%, from about 5% to about 40%, from about 5% to about 20%) by weight of a polymer, e.g., an ion-conducting polymer, and from about 5% to about 95% (e.g., from about 5% to about 75%, from about 5% to about 50%, from about 5% to about 30%) by weight of a plasticizer, from about 0.05 M to about 10 M of a redox electrolyte of organic or inorganic iodides (e.g., from about 0.05 M to about 5 M, from about 0.5 M to about 5 M, from about 1 to about 3 M), and from about 0.01 M to about 1 M (e.g., from about 0.05M to about 0.5 M, from about 0.05 M to about 0.2 M, from about 0.05 M to about 0.15 M) of iodine. The ion-conducting polymer may include, for example, polyethylene oxide (PEO), polyacrylonitrile (PAN), polymethylmethacrylate (PMMA), polyethers, and polyphenols. Examples of plasticizers include ethyl carbonate, propylene carbonate, mixtures of carbonates, organic phosphates, butyrolactone, and dialkylphthalates.

Charge carrier layer 140 typically includes a redox system. Suitable redox systems may include organic and/or inorganic redox systems. Examples of such systems include cerium(III) sulphate/cerium(IV), bromide/bromine, iodide/iodine (e.g., containing dialkylimidazolium iodide), $Fe^{2+}/Fe^{3+}$, $Co^{2+}/Co^{3+}$, and viologens. Furthermore, an electrolyte solution may have the formula $M_iX_j$, where i and j are greater than or equal to one, where X is an anion, and M is lithium, copper, barium, zinc, nickel, a lanthanide, cobalt, calcium, aluminum, or magnesium. Suitable anions include chloride, for example, perchlorate, thiocyanate, trifluoromethyl sulfonate, and hexafluorophosphate.

In some embodiments, the zwitterionic compound(s) can form a complex with constituents of the charge carrier material and/or the redox material (e.g., to form an ionic liquid or an ionic glass). For example, zwitterionic material(s) can be complexed with one or more lithium salts. In certain embodiments, the zwitterionic compound(s) can be mixed with a lithium salt, and then an iodide compound (e.g., dialkylimidazolium iodide) is added. Typically, one or more passivating agents (e.g., tertiary butyl pyridine, N-methyl benimidazole) and iodine are also present.

Generally, a solvent is also contained within charge carrier layer 140. Examples of solvents include GBL, propylene, ethylene carbonate, NMP, DMF, DMSO, sulfolane, cyclic carbonates, lactones and lactams.

In some embodiments, charge carrier layer 140 includes at least about 10 volume fraction (e.g., at least about 15 volume fraction, at least about 20 volume fraction, at least about 25 volume fraction) and/or at most about 60 volume fraction (e.g., at most about 55 volume fraction, at most about 50 volume fraction, at most about 45 volume fraction) of a zwitterionic compound-lithium salt complex, and from about 10 weight percent to about 60 weight percent of dialkylimidazolium iodide. In certain embodiments, charge carrier layer 140 can include at least about five volume fraction (e.g., at least about 10 volume fraction, at least about 20 volume fraction, at least about 30 volume fraction) and/or at most about 70 volume fraction (e.g., at most about 60 volume fraction, at most about 50 volume fraction) solvent.

Charge carrier layer 140 containing one or more zwitterionic compounds can have a relatively high transference number.

Turning now to other components of DSSC 100, layer 130 is generally formed of a material that can catalyze a redox reaction in charge carrier layer 140. Examples of materials from which layer 130 can be formed include platinum and poly(3,4-ethelynedioxythiophene) (PEDOT). PEDOT layers are discussed in U.S. Ser. No. 60/495,302, filed on Aug. 15, 2003, and U.S. Ser. No. 10/897,268, filed Jul. 22, 2004, both of which are hereby incorporated by reference.

The composition and thickness of electrically conductive layer 120 is generally selected based on desired electrical conductivity, optical properties, and/or mechanical properties of the layer. In some embodiments, layer 120 is transparent. Examples of transparent conductors suitable for forming such a layer include certain metal oxides, such as indium tin oxide (ITO), tin oxide, and a fluorine-doped tin oxide. Electrically conductive layer 120 may be, for example, between about 100 nm and 500 nm thick, (e.g., between about 150 nm and 300 nm thick).

In embodiments where counter electrode 111 is not transparent, electrically conductive layer 120 can be opaque (i.e., can transmit less than about 10% of the visible spectrum energy incident thereon). For example, layer 120 can be formed from a continuous layer of an opaque metal, such as copper, aluminum, indium, or gold.

Figure 2:
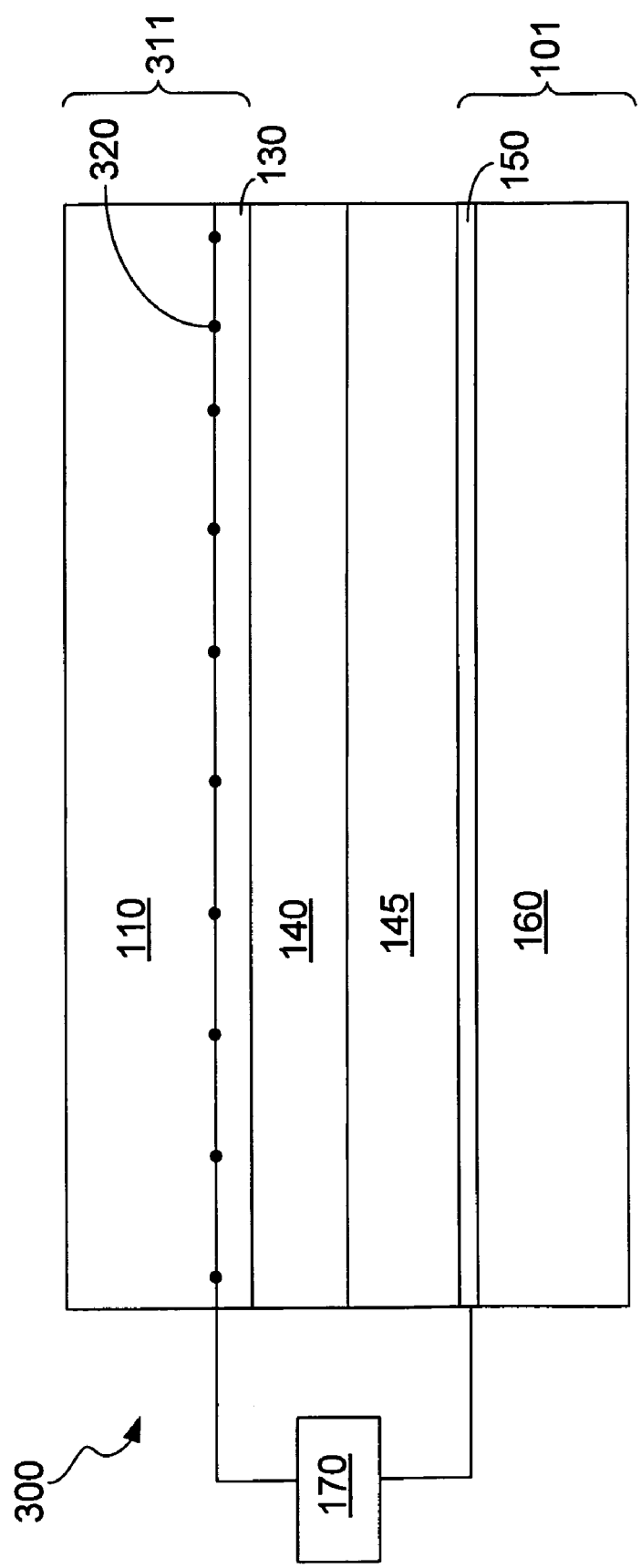
FIG. 2 is a cross-sectional view of an embodiment of a photovoltaic cell having a mesh electrode.

In some embodiments, electrically conductive layer 120 can include a discontinuous layer of a conductive material. For example, electrically conductive layer 120 can include an electrically conducting mesh. Referring to FIG. 2, a counter electrode 311 of a DSSC 300 includes a mesh electrode 320. Suitable mesh materials include metals, such as palladium, titanium, platinum, stainless steels and allows thereof. In some embodiments, the mesh material includes a metal wire. The electrically conductive mesh material can also include an electrically insulating material that has been coated with an electrically conducting material, such as a metal. The electrically insulating material can include a fiber, such as a textile fiber or optical fiber. Examples of fibers include synthetic polymeric fibers (e.g., nylons) and natural fibers (e.g., flax, cotton, wool, and silk). The mesh electrode can be flexible to facilitate, for example, formation of the DSSC by a continuous manufacturing process.

The mesh electrode may take a wide variety of forms with respect to, for example, wire (or fiber) diameters and mesh densities (i.e., the number of wires (or fibers) per unit area of the mesh). The mesh can be, for example, regular or irregular, with any number of opening shapes. Mesh form factors (such as, e.g., wire diameter and mesh density) can be chosen, for example, based on the conductivity of the wire (or fibers) of the mesh, the desired optical transmissivity, flexibility, and/or mechanical strength. Typically, the mesh electrode includes a wire (or fiber) mesh with an average wire (or fiber) diameter in the range from about one micron to about 400 microns, and an average open area between wires (or fibers) in the range from about 60% to about 95%. Mesh electrodes are discussed in Published U.S. patent application Ser. No. 2003/0230337, filed Mar. 24, 2003 and published Dec. 18, 2003, which is hereby incorporated by reference.

Substrate 110 can be formed from a mechanically-flexible material, such as a flexible polymer, or a rigid material, such as a glass. Examples of polymers that can be used to form a flexible substrate include polyethylene naphthalates (PEN), polyethylene terephthalates (PET), polyethyelenes, polypropylenes, polyamides, polymethylmethacrylate, polycarbonate, and/or polyurethanes. Flexible substrates can facilitate continuous manufacturing processes such as web-based coating and lamination.

The thickness of substrate 110 can vary as desired. Typically, substrate thickness and type are selected to provide mechanical support sufficient for the DSSC to withstand the rigors of manufacturing, deployment, and use.

Substrate 110 can have a thickness of from about 50 to about 5,000 microns, such as, for example, from about 100 to about 1,000 microns.

In embodiments where the counter electrode is transparent, substrate 110 is formed from a transparent material. For example, substrate 110 can be formed from a transparent glass or polymer, such as a silica-based glass or a polymer, such as those listed above. In such embodiments, electrically conductive layer 120 should also be transparent.

Substrate 160 and electrically conductive layer 150 can be similar to substrate 110 and electrically conductive layer 120, respectively. For example, substrate 160 can be formed from the same materials and can have the same thickness as substrate 110. In some embodiments however, it may be desirable for substrate 160 to be different from 110 in one or more aspects. For example, where the DSSC is manufactured using a process that places different stresses on the different substrates, it may be desirable for substrate 160 to be more or less mechanically robust than substrate 110. Accordingly, substrate 160 may be formed from a different material, or may have a different thickness that substrate 110. Furthermore, in embodiments where only one substrate is exposed to an illumination source during use, it is not necessary for both substrates and/or electrically conducting layers to be transparent. Accordingly, one of substrates and/or corresponding electrically conducting layer can be opaque.

As discussed previously, photosensitized layer 145 includes a semiconductor material and a photosensitizing agent. These component materials can be in the form of a photosensitized nanoparticle material, a heterojunction composite material, or combinations thereof.

Suitable heterojunction composite materials include fullerenes (e.g., $C_{60}$), fullerene particles, or carbon nanotubes. The heterojunction composite material may be dispersed in polythiophene or some other hole transport material. In various embodiments, the heterojunction composite material includes fullerene particles and/or aggregates of fullerene particles that have an average size of between about 14 nm and 500 nm. Other examples of suitable heterojunction composite materials are composites including conjugated polymers, such as polyphenylene vinylene, in conjunction with non-polymeric materials. Typically, where photosensitized layer 145 includes a heterojunction composite material, the layer is between about 0.1 microns and about 20 microns thick.

Suitable nanoparticles include nanoparticles of the formula $M_xO_y$, where M may be, for example, titanium, zirconium, tungsten, niobium, lanthanum, tantalum, terbium, or tin and x and y are integers greater than zero. Other suitable nanoparticle materials include sulfides, selenides, tellurides, and oxides of titanium, zirconium, tungsten, niobium, lanthanum, tantalum, terbium, tin, or combinations thereof. For example, $TiO_2$, $SrTiO_3$, $CaTiO_3$, $ZrO_2$, $WO_3$, $La_2O_3$, $Nb_2O_5$, $SnO_2$, sodium titanate, cadmium selenide (CdSe), cadmium sulphides, and potassium niobate may be suitable nanoparticle materials. In various embodiments, photosensitized layer 145 includes nanoparticles with an average size between about two nm and about 100 nm (e.g., between about 10 nm and 40 nm, such as about 20 nm).

The nanoparticles can be interconnected, for example, by high temperature sintering, or by a reactive polymeric linking agent, such as poly(n-butyl titanate). A polymeric linking agent can enable the fabrication of an interconnected nanoparticle layer at relatively low temperatures (e.g., less than about 300° C.) and in some embodiments at room temperature. The relatively low temperature interconnection process may be amenable to continuous manufacturing processes using polymer substrates.

The interconnected nanoparticles are photosensitized by a photosensitizing agent. The photosensitizing agent facilitates conversion of incident light into electricity to produce the desired photovoltaic effect. It is believed that the photosensitizing agent absorbs incident light resulting in the excitation of electrons in the photosensitizing agent. The energy of the excited electrons is then transferred from the excitation levels of the photosensitizing agent into a conduction band of the interconnected nanoparticles. This electron transfer results in an effective separation of charge and the desired photovoltaic effect. Accordingly, the electrons in the conduction band of the interconnected nanoparticles are made available to drive external load 170.

The photosensitizing agent can be sorbed (e.g., chemisorbed and/or physisorbed) on the nanoparticles. The photosensitizing agent may be sorbed on the surfaces of the nanoparticles, within the nanoparticles, or both. The photosensitizing agent is selected, for example, based on its ability to absorb photons in a wavelength range of operation (e.g., within the visible spectrum), its ability to produce free electrons (or electron holes) in a conduction band of the nanoparticles, and its effectiveness in complexing with or sorbing to the nanoparticles. Suitable photosensitizing agents may include, for example, dyes that include functional groups, such as carboxyl and/or hydroxyl groups, that can chelate to the nanoparticles, e.g., to Ti(IV) sites on a $TiO_2$ surface. Exemplary dyes include anthocyanines, porphyrins, phthalocyanines, merocyanines, cyanines, squarates, eosins, and metal-containing dyes such as cis-bis (isothiocyanato)bis(2,2'-bipyridyl-4,4'-25 dicarboxylato)-ruthenium (II) ("N3 dye"), tris(isothiocyanato)-ruthenium (II)-2,2':6',2''-terpyridene-4,4',4''-tricarboxylic acid, cis-bis (isothiocyanato)bis(2,2'-bipyridyl-4,4'-dicarboxylato) ruthenium (II) bis- tetrabutylammonium, cis-bis(isocyanato) (2,2'-bipyridyl-4,4' dicarboxylato) ruthenium (II)and tris(2, 2'-bipyridyl-4,4'-dicarboxylato) ruthenium (II) dichloride, all of which are available from Solaronix.

Although, in the foregoing embodiments, the materials in charge carrier layer 140 are described as being in a layer that is distinct from the materials in photosensitized layer 145, in some embodiments, one or more materials of layer 140 can be at least partially disposed (intermixed with) the materials in photosensitized layer 145. In some embodiments, the materials of layers 140 and 145 can be interspersed in a composite layer.

In general, a zwitterionic compound can be formed by reacting with heating a heterocyclic nitrogen compound or a trialkylamine compound with an alkylating compound in the presence of a solvent (e.g., acetone, acetonitrile, dimethylformamide).

The following examples are illustrative and not intended to be limiting.

EXAMPLE 1

1-methyl-3-(4-sulfoxybutyl)methylimidazolium zwitterion was prepared as follows.

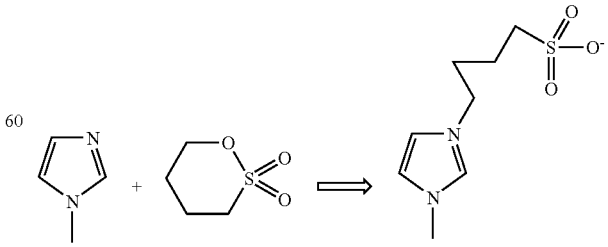

A one liter round bottom flask, equipped with a condenser, $N_2$ inlet, magnetic stirrer and a feeding funnel was charged with 200 mL of acetone and 15.07 grams (0.184 moles) of 1-methylimidazole. The flask was cooled to 0° C. in an ice bath and the slow, dropwise addition of a solution of 25 grams (0.184 moles) of 1,4-butane sulfone in 200 mL of acetone was started. After the addition, the ice bath was removed and the reaction mixture was stirred for 5 days.

The product was precipitated from acetone and separated by suction filtration. It was washed on the funnel with 2×200 mL of acetone and vacuum dried overnight at 60° C.

The $^1$H NMR of the product was: 9.15 ppm (1H, s), 7.75 ppm, (1H, s), 7.70 ppm, (1H, s), 4.20 ppm, (2H, t), 3.85 ppm,(3H, s), 2.45 ppm, (2H, t), 1.90 ppm, (2H, m), 1.55, (2H, m), using deuterated dimethylsulfoxide as the solvent.

The melting point of the product was 235° C.–237° C.

EXAMPLE

N-(2,2,2-trifluoroethyl)-2-(1-methyl-3-imidazolium)ethylsulfonamide was prepared as follows.

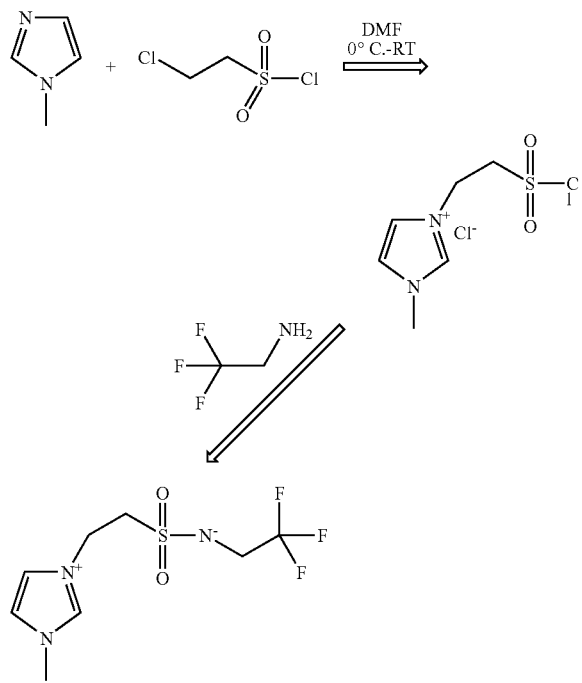

1-(2-chlorosulfonyl-ethyl)-3-methylimidazolium chloride was prepared as follows. A round bottom flask, equipped with a condenser, feeding funnel, a magnetic stirrer and a $N_2$ inlet was charged with 10.1 grams (0.122 moles) of 1-methylimidazole and 100 mL of DMF. The flask was cooled to 0° C. in an ice bath and the dropwise addition of 25 grams (0.153 moles) of 2-chloro-1-ethanesulfonyl chloride was started. After the addition, the ice bath was removed and the mixture was allowed to react at room temperature for 3 days. The product was isolated by evaporating DMF on a rotavap and purified by dispersing it in ethyl ether twice. It was left under vacuum to dry overnight at RT.

10 grams (40.7 mmoles) of 1-(2-Chlorosulfonyl-ethyl)-3-methylimidazolium chloride and 3.26 grams (81.4 mmoles) of sodium hydroxide were dissolved in 60 mL of deionized water, and 5.0 grams (50.5 mmoles) of 2,2,2-trifluoroethylamine were added and stirred for three days. The product was purified by dissolving in ethanol and filtering off the precipitants. Ethanol was evaporated and the product was dissolved in 200 mL of water and extracted first with 5×250 mL ethyl ether and then with 5×60 mL ethyl acetate. The water was evaporated on the rotavap and the residue was dissolved in minimum amount of ethanol and reprecipitated in 200 mL ethyl acetate. The precipitate was collected by suction filtation and dried at 60° C. under vacuum overnight.

The $^1$H NMR spectrum of the product was: 2.5 ppm, (2H, s), 3.0 ppm, (2H, t), 3.8 ppm, (3H, s), 4.4 ppm (2H, t), 7.65 ppm (1H, s), 7.80 (1H, s), 9.15 ppm, (1H, s), using deuterated dimethylsulfoxide as the solvent.

EXAMPLE 3

An electrolyte solution was prepared as follows.

1.67 grams of viscous zwitterionic liquid obtained by complexing 5.0 grams (0.023 moles) of methyl-3-(4-sulfoxybutyl)methylimidazolium zwitterions with 6.6 grams of lithium bis(trifluoromethanesulfonyl) imide was added to 5 grams of g-butyrolactone to form a clear solution. To this was added 0.6 M of 1-methyl-3-butyl imidazolium iodide, 0.5 M of t-butyl pyridine and 0.1 M 0f iodine.

This electrolyte solution was incorporated in flexible dye sensitized solar cell. A 12 micron thick nanoporous titanium oxide coating was deposited on metal foil and was sintered at 450° C. for 30 minutes. The sintered titanium oxide film was sensitized with a ruthenium based Z907 dye. A flexible dye sensitized solar cell was fabricated by placing the electrolyte between the dye sensitized titanium oxide coated metal foil and a platinum catalyst coated indium-tin-oxide coated polyester film using a 25 mm thick hot melt adhesive (Surlyn 1702). A solar conversion efficiency of 5.2% was measured at 100 mW/cm2 solar irradiation from the fabricated flexible DSSC.

EXAMPLE 4

An electrolyte solution was prepared as follows. 0.6 M of 1-methyl-3-butyl imidaxazolium iodide, 0.5 M of t-butyl pyridine and 0.1 M of iodine were dissolved in g-butyrolactone.

This electrolyte solution was incorporated in a flexible dye sensitized solar cell using the procedure described in Example 3. An efficiency of 4.4% was measured at 100 mW/cm2 solar irradiation.

Other embodiments are in the claims.

What is claimed is:
1. A zwitterionic compound having the formula:

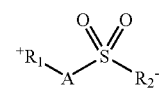

wherein:
$R_2$ is an anionic moiety that comprises:

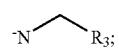

$R_1$ is a cationic heterocyclic moiety, a cationic ammonium moiety, a cationic guanidinium moiety, or a cationic phosphonium moiety;
A is $(C(R_3)_2)_n$;
n is zero or greater;

each $R_3$ is independently H, halo, or a carbon-containing moiety selected from the group consisting of $C_x$ alkyl, cycloalkyl, heterocyclyl, $C_{x+1}$ alkenyl, $C_{x+1}$ alkynyl and aryl, the carbon-containing moiety optionally being substituted with one or more halo; and x is at least 1.

2. The zwitterionic compound of claim 1, wherein n is at least 1.

3. The zwitterionic compound of claim 2, wherein n is at most 20.

4. The zwitterionic compound of claim 2, wherein n is at most 10.

5. The zwitterionic compound of claim 2, wherein n is at most 5.

6. The zwitterionic compound of claim 1, wherein x is at most 20.

7. The zwitterionic compound of claim 6, wherein x is at most 15.

8. The zwitterionic compound of claim 6, wherein x is at most 10.

9. The zwitterionic compound of claim 1, wherein $R_1$ comprises a cationic nitrogen-substituted heterocyclic moiety.

10. The zwitterionic compound of claim 9, wherein the cationic nitrogen-substituted heterocyclic moiety includes at least two nitrogen atoms.

11. The zwitterionic compound of claim 1, wherein $R_1$ comprises a cationic substituted ammonium moiety.

12. The zwitterionic compound of claim 11, wherein the cationic substituted ammonium moiety comprises an alkyl substituted cationic ammonium moiety.

13. The zwitterionic compound of claim 1, wherein $R_1$ comprises a cationic substituted guanidinium moiety.

14. The zwitterionic compound of claim 1, wherein:

$R_1$ is a cationic nitrogen-substituted heterocyclic moiety, a cationic alkyl substituted ammonium moiety, a cationic guanidinium moiety, or a cationic phosphonium moiety; and each $R_3$ is independently H, halo, or a $C_1$–$C_6$ alkyl that is optionally substituted with one or more halo.

15. The zwitterionic compound of claim 1, wherein:

n is 1–4;

$R_1$ is an alkyl imidazolium, piperidinium, pyridinium, morpholinium, pyrimidinium, pyridazinium, pyrazinium, pyrazolium, pyrrolinium, thiazolium, oxazolium, triazolium pentalkyl guanidinium, or asymmetric tetraalkylammonium; and each $R_3$ is independently H, F, or a $C_1$–$C_6$ alkyl that is optionally substituted with one or more F.

16. The zwitterionic compound of claim 1, wherein:

n is 1–4;

$R_1$ is alkyl imidazolium, pyridinium, pyridazinium, or pyrazinium; and $R_3$ is a Me that is optionally substituted with one or more F.

17. The zwitterionic compound of claim 1, wherein:

n is 2 or 3;

$R_1$ is alkyl imidazolium; and $R_3$ is $CF_3$.

18. The zwitterionic compound of claim 1, wherein the compound has the formula:

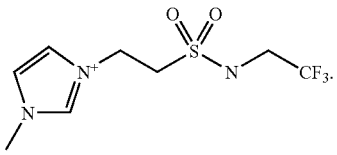

19. A photovoltaic cell, comprising:

a first electrode;

a second electrode; and a charge carrier layer between the first and second electrodes, the charge carrier layer comprising:

an electrolyte; and a zwitterionic compound having the formula:

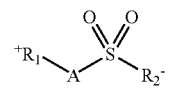

wherein:

$R_2$ is an anionic moiety that comprises:

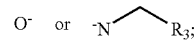

$R_1$ is a cationic heterocyclic moiety, a cationic ammonium moiety, a cationic guanidinium moiety, or a cationic phosphonium moiety;

A is $(C(R_3)_2)_n$;

n is zero or greater;

each $R_3$ is independently H, halo, or a carbon-containing moiety selected from the group consisting of $C_x$ alkyl, cycloalkyl, heterocyclyl, $C_{x+1}$ alkenyl, $C_{x+1}$ alkynyl and aryl, the carbon-containing moiety optionally being substituted with one or more halo; and x is at least 1.

20. The photovoltaic cell of claim 19, wherein the electrolyte comprises a lithium salt.

21. The photovoltaic cell of claim 19, further comprising a redox system.

22. The photovoltaic cell of claim 21, wherein the electrolyte comprises a lithium salt.

23. The photovoltaic cell of claim 21, wherein the electrolyte and zwitterionic compound form a complex.

24. The photovoltaic cell of claim 23, wherein the charge carrier layer comprises at least about 10 volume fraction of the complex.

25. The photovoltaic cell of claim 24, wherein the charge carrier layer comprises at most about 60 volume fraction of the complex.

26. The photovoltaic cell of claim 21, wherein the charge carrier layer comprises at least about 10 volume fraction of the redox system.

27. The photovoltaic cell of claim 26, wherein the charge carrier layer comprises at most about 60 volume fraction of the redox system.

28. The photovoltaic cell of claim 21, further comprising a solvent.

29. The photovoltaic cell of claim 28, wherein the charge carrier layer comprises at least about five volume fraction of the solvent.

30. The photovoltaic cell of claim 29, wherein the charge carrier layer comprises at most about 70 volume fraction of the solvent.

31. The photovoltaic cell of claim 19, further comprising a solvent.

32. The photovoltaic cell of claim 19, wherein n is at least 1.

33. The photovoltaic cell of claim 32, wherein n is at most 20.

34. The photovoltaic cell of claim 32, wherein n is at most 10.

35. The photovoltaic cell of claim 32, wherein n is at most 5.

36. The photovoltaic cell of claim 19, wherein x is at most 20.

37. The photovoltaic cell of claim 36, wherein x is at most 15.

38. The photovoltaic cell of claim 36, wherein x is at most 10.

39. The photovoltaic cell of claim 19, wherein $R_1$ comprises a cationic nitrogen-substituted heterocyclic moiety.

40. The photovoltaic cell of claim 39, wherein the cationic nitrogen-substituted heterocyclic moiety includes at least two nitrogen atoms.

41. The photovoltaic cell of claim 19, wherein $R_1$ comprises a cationic substituted ammonium moiety.

42. The photovoltaic cell of claim 41, wherein the cationic substituted ammonium moiety comprises a cationic alkyl substituted ammonium moiety.

43. The photovoltaic cell of claim 19, wherein $R_1$ comprises a cationic substituted guanidinium moiety.

44. The photovoltaic cell of claim 19, wherein:
$R_1$ is a cationic nitrogen-substituted heterocyclic moiety, a cationic alkyl substituted ammonium moiety, a cationic guanidinium moiety, or a cationic phosphonium moiety; and
each $R_3$ is independently H, halo, or $C_1$–$C_6$ alkyl that is optionally substituted with one or more halo.

45. The photovoltaic cell of claim 19, wherein:
n is 1–4;
$R_1$ is an alkyl imidazolium, piperidinium, pyridinium, morpholinium, pyrimidinium, pyridazinium, pyrazinium, pyrazolium, pyrrolinium, thiazolium, oxazolium, triazolium pentalkyl guanidinium, or asymmetric tetraalkylammonium; and
each $R_3$ is independently H, F, or $C_1$–$C_6$ alkyl that is optionally substituted with one or more F.

46. The photovoltaic cell of claim 19, wherein:
n is 1–4;
$R_1$ is alkyl imidazolium, pyridinium, pyridazinium, or pyrazinium; and $R_3$ is a Me that is optionally substituted with one or more F.

47. The photovoltaic cell of claim 19, wherein:
n is 2 or 3;
$R_1$ is alkyl imidazolium; and
$R_3$ is $CF_3$.

48. The photovoltaic cell of claim 19, wherein the zwitterionic compound has the formula:

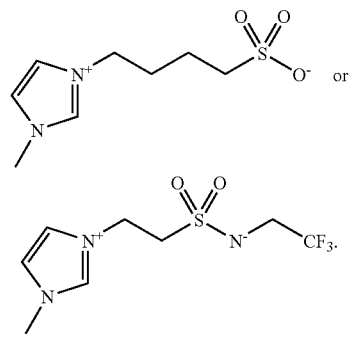

49. The photovoltaic cell of claim 19, wherein the electrolyte and zwitterionic compound form a complex.

50. The photovoltaic cell of claim 49, wherein the charge carrier layer comprises at least about 10 volume fraction of the complex.

51. The photovoltaic cell of claim 50, wherein the charge carrier layer comprises at most about 60 volume fraction of the complex.

52. The photovoltaic cell of claim 49, further comprising a redox system and a solvent.

53. The photovoltaic cell of claim 52, wherein the charge carrier layer comprises at least about five volume fraction of the solvent.

54. The photovoltaic cell of claim 53, wherein the charge carrier layer comprises at most about 70 volume fraction of the solvent.

55. The photovoltaic cell of claim 19, wherein the charge carrier layer comprises at least about 10 volume fraction of the redox system.

56. The photovoltaic cell of claim 55, wherein the charge carrier layer comprises at most about 60 volume fraction of the redox system.

57. The photovoltaic cell of claim 19, further comprising a solvent.

* * * * *

UNITED STATES PATENT AND TRADEMARK OFFICE
CERTIFICATE OF CORRECTION

PATENT NO. : 7,220,914 B2 Page 1 of 1
APPLICATION NO. : 11/000276
DATED : May 22, 2007
INVENTOR(S) : Kethinni G. Chittibabu, Savvas Hadjikyriacou and David Waller It is certified that error appears in the above-identified patent and that said Letters Patent is hereby corrected as shown below:

Column 1, Line 20, please insert:

--STATEMENT REGARDING FEDERALLY SPONSORED RESEARCH

This invention was made with Government support under Contract Number N00014-03-C-0428 awarded by the Department of the Navy. The Government has certain rights in the invention.--

Signed and Sealed this

Tenth Day of July, 2007

JON W. DUDAS
*Director of the United States Patent and Trademark Office*